(12) United States Patent
Burrows et al.

(10) Patent No.: US 7,416,588 B2
(45) Date of Patent: Aug. 26, 2008

(54) FLUID PURIFICATION

(75) Inventors: John Allen Burrows, Solihull (GB); John David Yair, Hagley (GB)

(73) Assignee: Brandenburg UK Limited, West Midlands (GB)

( * ) Notice: Subject to any disclaimer, the term of this patent is extended or adjusted under 35 U.S.C. 154(b) by 502 days.

(21) Appl. No.: 10/512,904

(22) PCT Filed: May 1, 2003

(86) PCT No.: PCT/GB03/01890

§ 371 (c)(1),
(2), (4) Date: Feb. 28, 2005

(87) PCT Pub. No.: WO03/092751

PCT Pub. Date: Nov. 13, 2003

(65) Prior Publication Data

US 2005/0173352 A1   Aug. 11, 2005

(30) Foreign Application Priority Data

May 1, 2002   (GB)   ................................. 0209920.8

(51) Int. Cl.
*B01D 49/00* (2006.01)
(52) U.S. Cl. .......................................... 96/224; 422/24
(58) Field of Classification Search .................. 96/224; 422/24
See application file for complete search history.

(56) References Cited

U.S. PATENT DOCUMENTS

| | | |
|---|---|---|
| 3,757,495 A | 9/1973 | Sievers |
| 3,846,072 A | 11/1974 | Patterson |
| 4,210,429 A | 7/1980 | Golstein |
| 4,533,992 A | 8/1985 | Magar et al. |
| 4,694,179 A | 9/1987 | Lew et al. |
| 4,766,321 A | 8/1988 | Lew et al. |
| 4,786,812 A | 11/1988 | Humphreys |
| 5,112,370 A | 5/1992 | Gazzano |
| 5,216,251 A | 6/1993 | Matschke |
| 5,498,394 A | 3/1996 | Matschke |
| 5,505,904 A | 4/1996 | Haldinger et al. |
| 5,612,001 A | 3/1997 | Matschke |
| 5,833,740 A | 11/1998 | Brais |
| 5,874,741 A | 2/1999 | Matschke |
| 5,997,619 A | 12/1999 | Knuth et al. |
| 6,022,511 A | 2/2000 | Matschke |

(Continued)

FOREIGN PATENT DOCUMENTS

DE   32 08 519   9/1983

(Continued)

*Primary Examiner*—Robert A Hopkins
(74) *Attorney, Agent, or Firm*—Proskauer Rose LLP

(57) ABSTRACT

A fluid purification device is provided, which comprises a chamber having an inlet and an outlet, a fluid mover, such as a fan, which causes fluid to pass through the chamber from the inlet towards the outlet and four elongate UV-C light sources in an arrangement such that fluid passes along their length and such that each light source forms an elongate edge of a square prism. The volume of the chamber and the speed of fluid movement as caused by the fluid mover are such that the fluid has a residence time in the chamber of greater than 1.0 seconds. The device may in particular be used to purify air.

34 Claims, 6 Drawing Sheets

U.S. PATENT DOCUMENTS

| | | | |
|---|---|---|---|
| 6,053,968 A | 4/2000 | Miller | |
| 6,221,314 B1 | 4/2001 | Bigelow | |
| 6,228,327 B1 | 5/2001 | Matschke | |
| 6,322,614 B1 | 11/2001 | Tillmans | |
| 6,337,483 B1 | 1/2002 | Matschke | |
| 2003/0021721 A1* | 1/2003 | Hall ........................... | 422/4 |

FOREIGN PATENT DOCUMENTS

| | | |
|---|---|---|
| GB | 1 461 094 | 5/1974 |
| GB | 1 540 752 | 2/1976 |
| GB | 2 215 234 A | 9/1989 |
| GB | 2 215 234 B | 12/1991 |
| JP | S51-61763 | 5/1976 |
| JP | S62-027093 | 2/1987 |
| WO | 97/07831 | 3/1997 |
| WO | 00/20045 | 4/2000 |

* cited by examiner

FLUID PURIFICATION

This application claims priority to and benefit of international application PCT/GB03/01890, filed May 1, 2003, and to GB 0209920.8, filed May 1, 2002, the contents of each of which are incorporated herein by reference.

The present invention relates to fluid purification devices and to methods of fluid purification using such devices.

Fluid purification, for example air purification, by means of ultraviolet (UV) light is well known. UV-C (short wave) light having a wavelength of between 100 nm and 280 nm is generally used in such applications. In particular, germicidal UV-C light having a wavelength of from about 200 nm to about 288 nm may be used to kill airborne micro-organisms.

A variety of fluid purification, especially air purification, devices are available that attempt to cleanse the fluid of micro-organisms by irradiating the fluid with germicidal UV-C light. However, many such devices pass the fluid over the UV-C light sources in a transverse direction and therefore the length of time during which the fluid is exposed to a significant strength of UV-C light is relatively short. Consequently, the proportion of micro-organisms in the fluid that are exposed to a dose of germicidal UV-C light sufficient to kill is relatively low.

The problem of increasing the proportion of micro-organisms killed has been attempted to be solved in several devices. For example, the use of UV reflective inner surfaces inside the device has been proposed, in order to increase the level of UV radiation present in the device. Further, elongate UV light sources have been used in purification devices such that the fluid flows along the length of the light source so as to provide a greater exposure time to the UV radiation for each unit of fluid.

However, there remains a need for a fluid purification device that can effectively eliminate from a fluid a very high proportion of micro-organisms such as the anthrax pathogen, *bacillus anthracis*, which have a lethal UV-C dose of between 10 000 and 15 000 $\mu Wscm^{-2}$ in the vegetative form and up to three times this dose when in the spore phase.

The present invention provides a fluid purification device, which device comprises a chamber having an inlet and an outlet, a fluid mover and four elongate UV-C light sources, wherein said fluid mover causes fluid to pass through the chamber from the inlet towards the outlet, the volume of the chamber and the speed of the fluid movement caused by the fluid mover being such that the fluid has a residence time in the chamber of greater than 1.0 seconds and, said light sources being provided in the chamber in an arrangement such that the fluid passes along their length and such that each light source forms an elongate edge of a square prism.

Preferably, the four elongate UV-C light sources are of a wattage and a distance from the centre of the chamber such that the level of UV-C energy at any point within the chamber is 15000 $\mu Wscm^{-2}$ or more. The UV-C light sources may suitably be 15 W or 25 W input UV-C light sources.

In one embodiment, the UV-C light sources may be 25 W input UV-C light sources and these may be arranged so as to be at a distance from the centre of the chamber of 50 mm or less. By selecting appropriate wattage and distances from the centre of the chamber for the light sources and making use of the particular arrangement of four light sources required by the present invention a purification device can be obtained which has a consistently high level of UV-C radiation throughout and which is capable of up to 99.999% reduction of a variety of challenge organisms within 24 hours. The skilled man would be able, without difficulty to select a wattage for the light sources and a size for the chamber such that a particular minimum energy level, for example 15000 $\mu Wscm^{-2}$, throughout the chamber is achieved.

Preferably the elongate UV-C light sources are located close to the inner surface of the chamber. The UV-C light sources are preferably positioned 30 mm or less from the inner wall of the chamber, more preferably 25 mm or less, for example 20 mm or less. Accordingly, it is preferred that the wattage of the UV-C light sources and the size of the chamber are selected such that the UV-C light sources can be positioned both sufficiently close to the centre of the centre of the chamber so as to provide adequate UV-C radiation throughout the chamber, for example so that the level of UV-C energy at any point within the chamber is 15000 $\mu Wscm^{-2}$ or more, and relatively close to the inner wall of the chamber. This allows a device to be provided with improved efficiency for killing micro-organisms.

The four elongate UV-C light sources may be the same or different; preferably they are the same. UV-C light sources other than these four elongate UV-C light sources arranged such that the fluid passes along their length and such that each light source forms an elongate edge of a square prism may be included in the device, for example within the chamber. Such additional light sources may be the same or different to the four elongate UV-C light sources. Preferably such additional light sources are the same as the four elongate UV-C light sources.

The UV-C light sources in the device preferably emit germicidal UV-C light in the range of from 240 to 280 nm. It is preferred that the UV-C light sources have a peak emission in the range of from 250 to 260 nm. More preferably, the UV-C light sources have a radiation peak at about 254 nm, for example the UV-C light sources may suitably have a peak emission at 253.7 nm.

It is also preferred that the UV-C light sources are not vacuum UV sources. Preferably, the UV-C light sources do not emit in the range of from 170 nm to 200 nm, more preferably do not emit in the range of 160 nm to 220 nm, and most preferably do not produce any radiation at a wavelength below 240 nm. UV-C emissions in this region result in the production of monoatomic oxygen. This is undesirable because monoatomic oxygen bonds with $O_2$ in the atmosphere to produce ozone.

The UV-C light sources may suitably be mercury vapour lamps. The UV-C light sources may be any suitable elongate shape, for example they may be elongate with a substantially circular cross section.

The UV-C light sources may suitably be commercially available UV-C light sources such as substantially elongate UV-C lamps. For example, the UV-C light sources may suitably be selected from the Philips TUV range of low pressure mercury lamps, the Philips HTQ range of medium pressure mercury lamps, the Sylvania G-Range of UV-C light sources or a suitable array of light emitting diodes.

The UV-C light sources may be fixed in position such that each forms an elongate edge of a square prism by any suitable means. For example, each light source may be attached to the chamber by means of a bracket to ensure it stays in position.

The fluid mover may be any suitable type of device for causing the movement of fluid through the chamber. The fluid mover may suitably be a device that draws fluid through the chamber such as a fan or a pump. Preferably, the fluid mover is a fan; for example, the fluid mover may be a centrifugal type fan. The fan may suitably be driven by an electric motor. Preferably, the fan is selected so as to have low noise levels, for example the fan may have a noise output of less than or equal to 35 decibels.

Preferably, the speed of the fluid through the chamber, as controlled by the fluid mover, and the volume of the chamber are such that the fluid is treated by UV-C radiation for greater than 1.0 s, preferably 1.1 s or more. To achieve this the fluid mover, for example a fan, moves the fluid through the chamber at a slower speed than is conventionally used. Additionally, the arrangement of the UV-C light sources in the device of the present invention allows the fluid to be in contact with UV-C radiation for a longer period than conventional devices.

The speed used to achieve the desired UV-C treatment time will of course depend upon the volume of the chamber but may suitably be of the order of from 0.3 to 0.4 ms$^{-1}$. The skilled man would clearly be able to select suitable combinations of chamber volume and fluid mover, for example fan, speed so as to achieve the desired treatment time without difficulty. It is preferred that the fluid moves through the chamber at a rate such that it is treated by UV-C radiation for 1.2 s or more, more preferably 1.4 s or more, most preferably 1.5 s or more, for example 1.7 s or more.

It is preferred that the chamber has inner surfaces that are UV-C reflective; preferably, the inner surfaces reflect germicidal UV-C light. More preferably, the inner surface has a coefficient of reflection of 60% or more for germicidal UV-C wavelengths, more preferably 70% or more for example 85% or more. Suitably, the inner surface of the chamber may be aluminium, for example spun aluminium or aluminium alloy. The inner surface of the chamber may be provided with a suitable finish such as a mill finish.

Preferably, the fluid purification device includes one or more filters. More preferably, a filter is provided at or near the beginning of the fluid flow through the device. For example, a filter may suitably be provided at or immediately adjacent the inlet of the chamber, such that all fluid entering the chamber through the inlet subsequently passes through the filter.

Such a filter removes from the fluid most or all of the dirt and debris present in the fluid to reduce contamination of the chamber and thus reduce the possibility of the luminescence and reflectance of the chamber being unduly affected. In particular, the filter prevents or reduces the amount of dirt and debris settling on the UV-C light sources and thus ensures that the UV-C light sources are kept efficient and operate at design specifications, preferably for the life of the fluid purification device.

The filter may be any suitable filter as known in the art. Preferably, the filter has a mesh size such as to catch the majority of dirt and debris present in the fluid. However, the filter preferably has a mesh size such that the flow of microorganisms is not impeded. For example, the filter may have a mesh size of 13.8 pores/cm. The filter may be a removable filter or may be permanently attached to the device. Preferably the filter is removable in order to facilitate cleaning.

Preferably, the fluid purification device includes an outer casing within which the chamber is located. It is preferred that the outer casing is made of metal or plastics material.

The device may suitably include means as known in the art for reducing the level of UV light that escapes from the device, for example the device may include baffles.

The device may suitably be used to purify any fluid. Preferably, the device is used to purify a gas such as air or a liquid such as water.

The present invention also provides a method of reducing the level of microbial contaminants in a fluid which method comprises passing the fluid through a device according to the present invention, with the fan of the device causing the fluid to move through the device such that the fluid is irradiated with germicidal UV-C light from the UV-C light sources.

For the sake of clarity, throughout the specification, the term 'elongate edge of a square prism' refers to an edge of the prism which connects one corner of one square face of the prism with the corresponding corner of the opposite square face of the prism.

An embodiment of the present invention will now be described with reference to the drawings in which.

Figure 5:
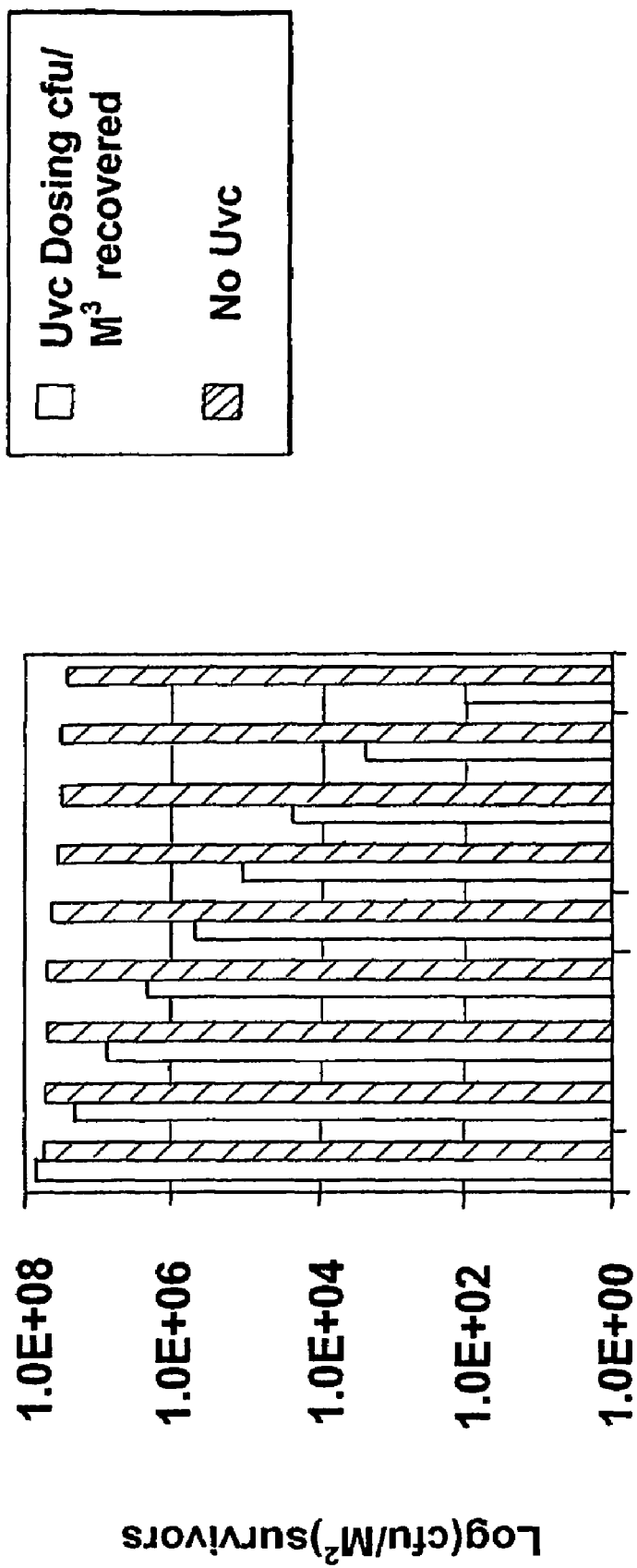
Figure 6:
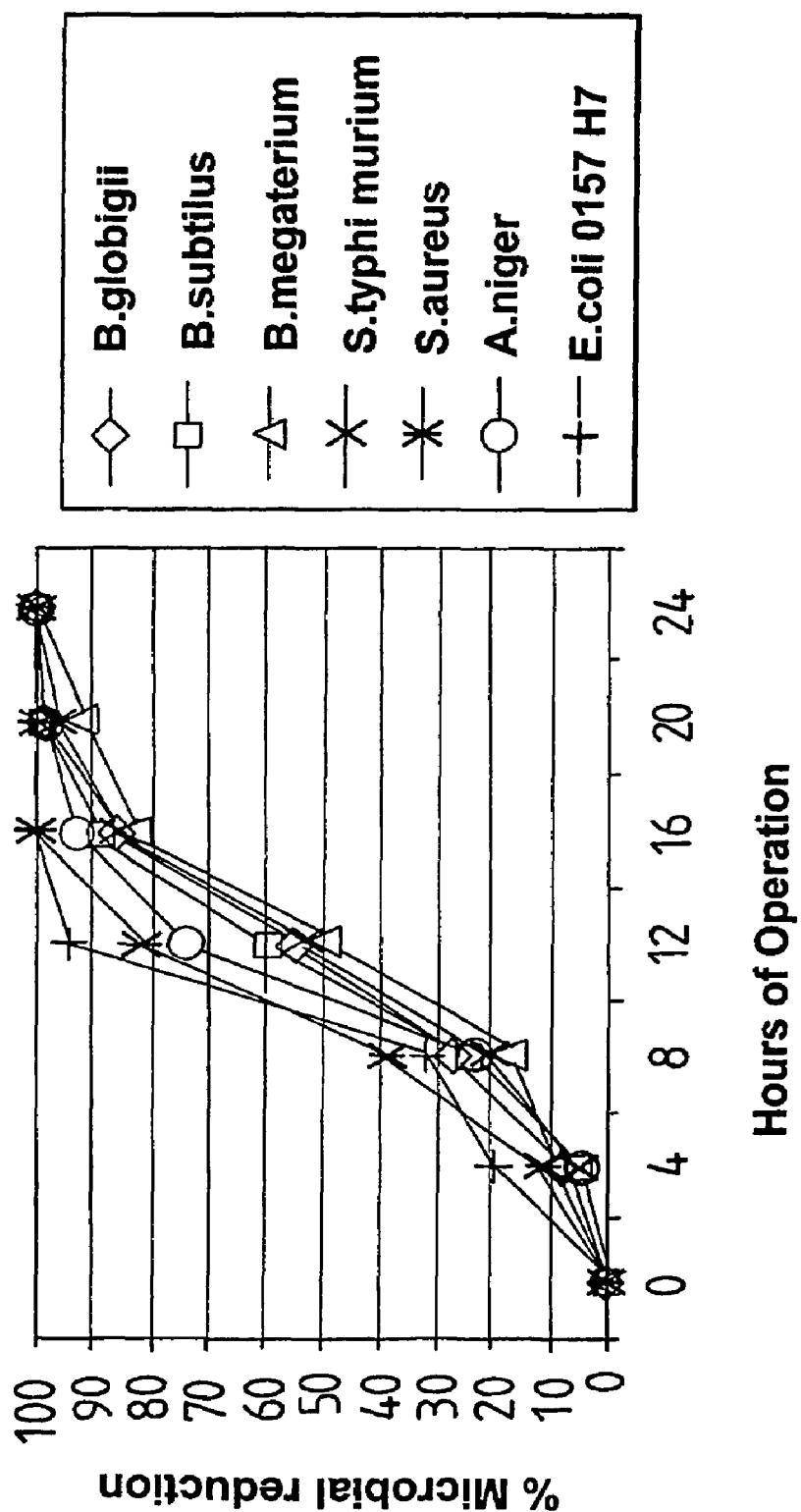

FIG. 5 is a graph showing the number of *Bacillus megaterium* spores in a closed system over 8 hours when the system is treated with a device according to the present invention and corresponds with the information shown in Table 3; and FIG. 6 is a graph showing the % reduction in airborne pathogens in a contained room space over 24 hours when the room space is treated with a device according to the present invention and corresponds with the information shown in Table 4.

The fluid purification device 1 is a device suitable for purifying air. The device 1 includes a purifying chamber 2 through which air to be purified is passed. The purifying chamber 2 is elongate with a truncated square cross-section, having a length of 516.0 mm, a width of 151.4 mm, a height of 151.4 mm, a cross sectional area of 217 cm$^2$ and a volume of 11198 cm$^3$. The purifying chamber is provided with an air inlet 3 at a first end of the chamber 2a and an air outlet 4 at a second end of the chamber 2b directly opposite the first end, such that in use air flows into the chamber 2 through inlet 3, along the length of the chamber 2 and out of the chamber 2 through outlet 4.

The purifying chamber 2 has an inner surface 5 made from aluminium, which reflects UV-C light. Located within the purifying chamber 2 are four elongate UV-C lamps 6 having 25 W input, a radiation peak of 253.7 mm and having an emission spectrum such that no radiation is produced below 240 nm. Each lamp 6 has a circular cross section of diameter 26.0 mm and a length of 416.0 mm, with the length of the lamp including end fittings being 450 mm.

The lamps 6 run along the length of the chamber 2 from the first end 2a to the second end 2b and therefore in use the air passing through the chamber flows along the length of the lamps 6. The lamps 6 are arranged within the chamber 2 such that each lamp forms one of the four elongate edges of a square prism. The lamps 6 are located so that the surface of each is approximately 50 mm from the centre of the chamber 2 and approximately 25 mm from the inner surface 5. The lamps 6 are each held in position by means of bracket 9 attached to the inner wall of chamber 2. In operation, the UV-C lamps 6 provide a minimum energy of 15000 μWs cm$^{-2}$ throughout the chamber 2.

At the first end 2a of the purifying chamber 2, adjacent the air inlet 3, is provided a fan 7. The fan 7 is powered by an electric motor (not shown) and in use causes air to move through the purifying chamber 2 from first end 2a to second end 2b, with the air entering the chamber 2 via air inlet 3 and exiting via air outlet 4. The fan 7 operates so as to move the air along the length of the chamber 2 at a speed of 0.3 ms$^{-1}$.

The purifying chamber 2 is provided with filter 10 at the first end 2a of the chamber. The filter 10 has a mesh size of 13.8 pores/cm and is located between air inlet 3 and fan 7 such that all air entering chamber 2 passes through the filter 10. The filter 10 traps airborne particles, thus minimising the amount of airborne dirt and debris entering the chamber 2 and so maintaining the efficiency of the device 1.

The chamber 2 is enclosed within outer casing 8. The outer casing is made of metal and includes means 11 for fastening the device 1 to a surface such as a wall. The airflow within device 1 is managed such that the outer casing 8 does not become hot in use and therefore the exterior of the device 1 can be touched.

EXAMPLES

The device as described above with reference to the drawings was tested in order to demonstrate its ability to purify air.

The organisms employed were as follows unless otherwise specified:
*Bacillus megaterium* NCTC 10342
*Bacillus globigii* ATCC 49822
*Bacillus subtilis* ATCC 19659
*Bacillus cereus* NCTC 2599
*Salmonella typhi murium* NCTC 74
*E. coli* 0157H7 NCTC 12079 (ATTENUATED STRAIN : EX PUBLIC HEALTH SERVICE CULTURE)
*Staphylococcus aureus* NCTC 8532
*Aspergilius niger* NCPF 2275

*Bacillus megaterium*, *bacillus globigii* and *bacillus subtilis* are known to be suitable *bacillus anthracis* surrogates, having similar UV-C susceptibility to that of *bacillus anthracis*.

Example 1

Volumetric Antimicrobial Performance

Trials were conducted in a microbiologically sealed PVC construction consisting of two chambers of identical dimension. These chambers were connected horizontally by the device of the present invention as detailed above. However, to permit uniform microbial dispersion and to facilitate study of microbial dynamics in the absence of UV-C doses, the device was modified so that the fan could be run with the lamp out of circuit. Atmosphere was transferred from the first chamber, A to the second chamber, B, by means of the fan incorporated in the device. An atmosphere return tube of 15 cm diameter also connected chambers A and B, giving an overall operating volume of 54 $m^3$.

Each chamber contained four floor mounted fans to assist with microbial dispersion and also a silica gel unit to prevent excessive humidity build up. All surfaces (excluding the internal surfaces of the device of the present invention) were sprayed with an anti static treatment. Pressure equalisation occurred via four apertures secured by 0.2 micron membrane filters. The construction was equipped both for the introduction of microbial aerosols (via chamber A) and for volumetric recovery of atmosphere in volumes of an appropriate diluent medium (via chamber B).

Prior to introduction of test organisms the lamp complex was run in circuit for 4 hours to eliminate airborne contamination resident within the system. Control plates showed that on all occasions this conditioning sterilisation action did reduce internal contamination to <10 cfu/$m^3$.

The test organisms *Bacillus globigii*, *Bacillus megaterium* and *Bacillus subtilis* were obtained as calibrated dry spore suspensions (powder) or as vegetative cultures. Spore suspensions were obtained by heat treatment (63.5° C. for 35 minutes) of mid exponential liquid cultures in brain heart infusion containing 1% starch. Heat treated cultures were then lyophilised and assayed. Assays were conducted daily on spore stocks to assure viability (viable titre by enumeration on TSA with confirmation) and vigour (impedance curve; onset of exponential growth and curve slope).

Test organisms in the form of spores were introduced and dispersed in chamber A by a positive air pressure jet while in the case of vegetative cultures dispersion was achieved by use of a fogging device delivering a particle size range of 5-15 micron. The target level of inoculation in all cases was in the 10 e7 cfu/$m^3$ range.

All studies were conducted over 8 hours and each study was repeated nine times over consecutive days. All organisms were studied in monoculture. Additionally, as it was predicted that spore precipitation would occur due to gravity or electrostatic attraction, monitoring exercises were conducted with the UV-C lamps out of circuit. Thus background lethality figures due to system artefacts were obtained and this data was employed to correct the lethality data obtained when the UV-C lamps were in operation.

Sampling was achieved by aspiration of a 1 $m^3$ atmosphere volume through 100 ml of diluent (peptone saline recovery broth) which formed the initial test dilution. Recovery of isolates was obtained by serial dilution and plating on appropriate agars. All analyses were conducted in duplicate with appropriate controls.

All isolates obtained were confirmed by prescribed biochemical and morphological characteristics.

Results

Figure 3:
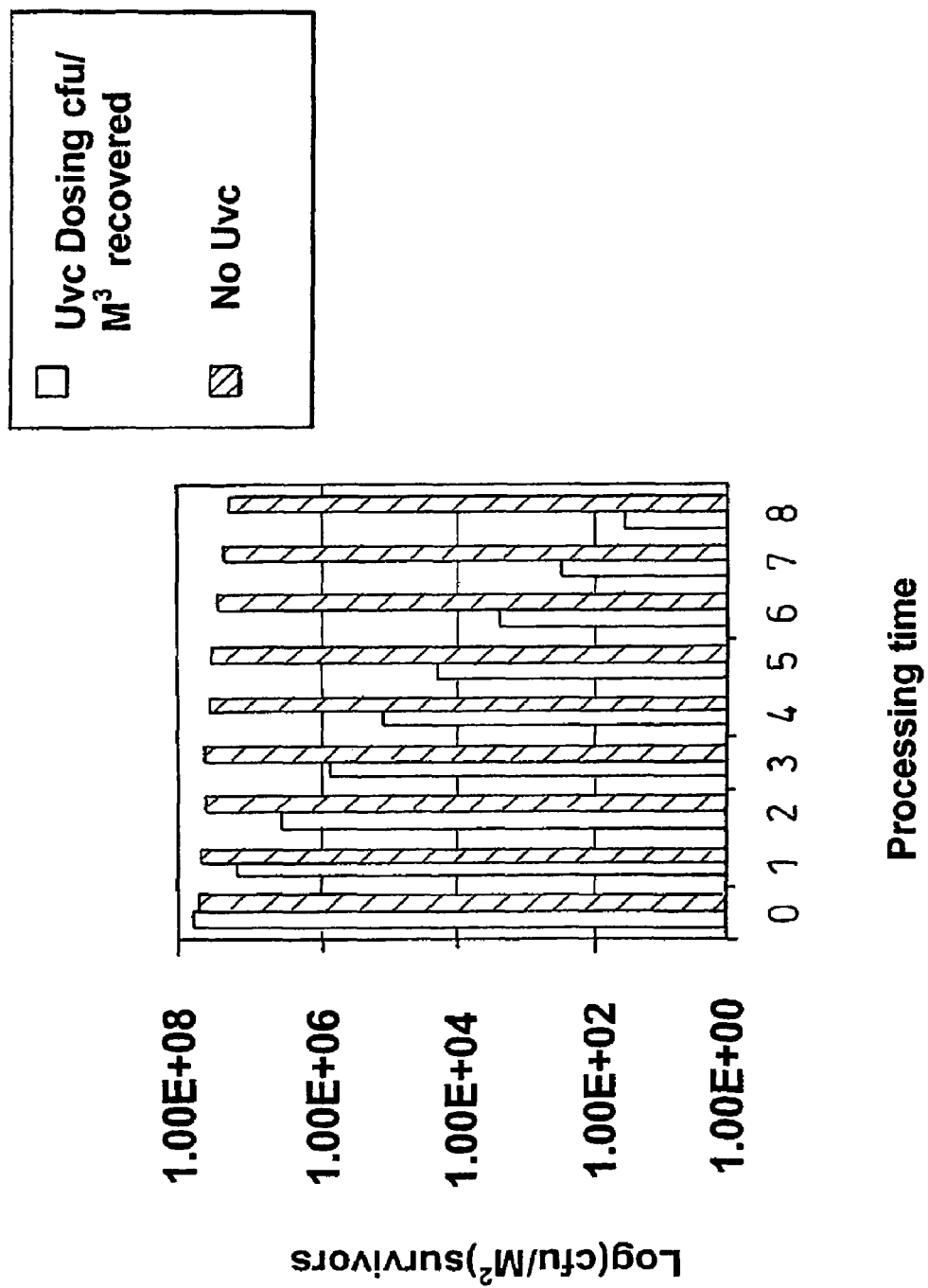
FIG. 3 is a graph showing the number of *Bacillus globigii* spores in a closed system over 8 hours when the system is treated with a device according to the present invention and corresponds with the information shown in Table 1.
Figure 4:
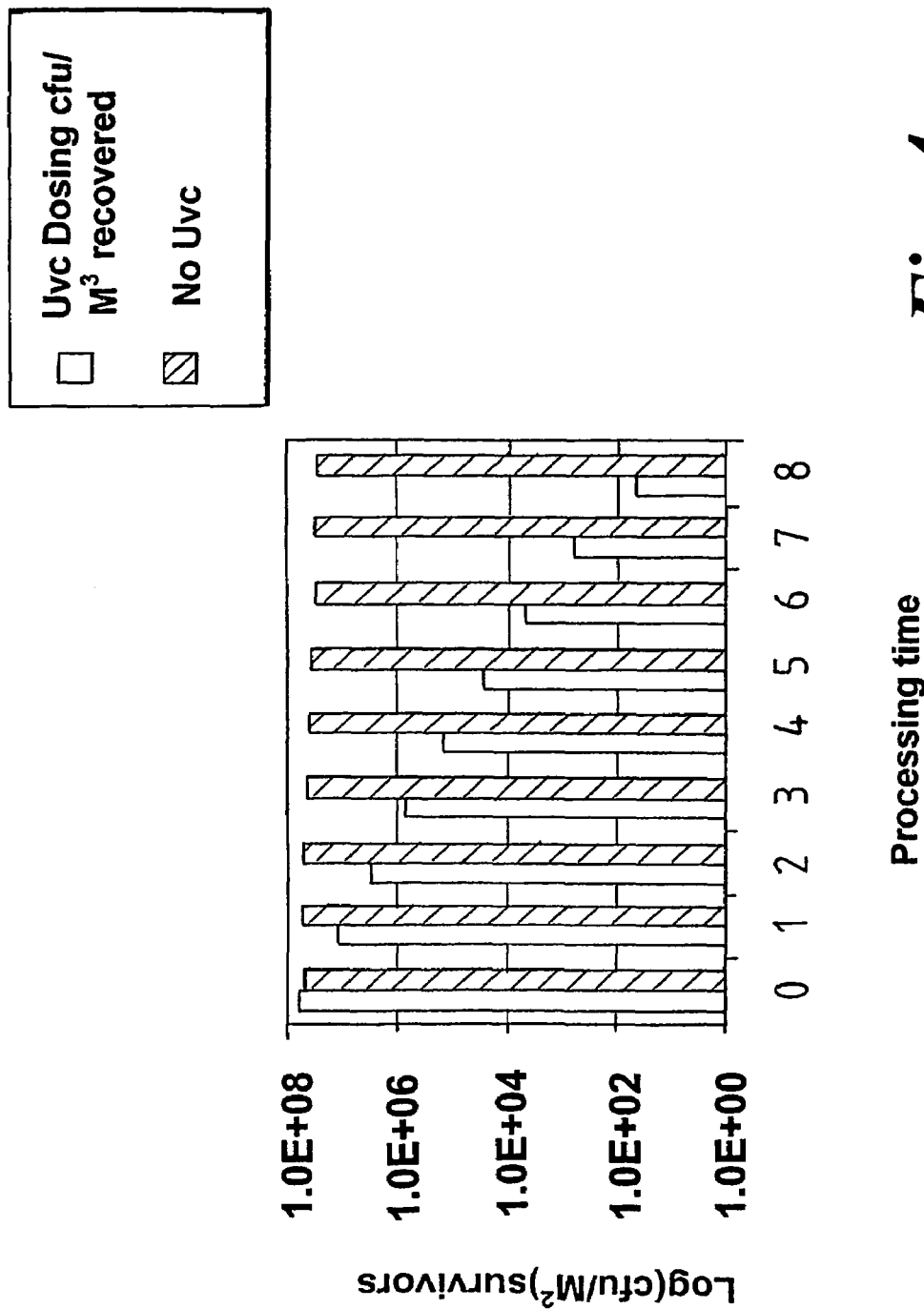
FIG. 4 is a graph showing the number of *Bacillus subtilis* spores in a closed system over 8 hours when the system is treated with a device according to the present invention and corresponds with the information shown in Table 2.

Tables 1-3 and the related FIGS. 3-5 summarise the mean data obtained for the 8 hour trial series for each test organism. Each table shows the results for microbial reduction purely due to precipitation or other system artefacts and with UV-C doses corrected for precipitation.

TABLE 1

Mean data for the recovery of *Bacillus globigii* in a 54 $m^3$ closed system over 8 hours with UV-C treatment by the device of the invention.

| Sample point in hours | Control Cfu/$m^3$ recovered | UV-C Dosing Cfu/$m^3$ recovered | Actual % kill % kill corrected for precipitation |
|---|---|---|---|
| 0 | 4.90E+07 | 5.60E+07 | 0.00 |
| 1 | 4.5E+07 | 1.50E+07 | 66.00 |
| 2 | 4.1E+07 | 3.56E+06 | 68.40 |
| 3 | 3.8E+07 | 7.26E+05 | 72.30 |
| 4 | 3.5E+07 | 1.22E+05 | 73.90 |
| 5 | 3.0E+07 | 1.88E+04 | 70.40 |
| 6 | 2.6E+07 | 2.27E+03 | 74.20 |
| 7 | 2.2E+07 | 2.68E+02 | 73.90 |
| 8 | 1.9E+07 | 3.40E+01 | 74.50 |

Overall % kill in 8 hours=99.9999%
Mean population precipitation rate=10.8% per hour
Mann-Whitney Test: *Bacillus globigii*
The median values for *Bacillus globigii* survival with no UV-C doses and UV-C doses differ significantly
The two-tailed P value is 0.0400 which is considered significant
The P value is exact.
Mann-Whitney U-statistic=17.000
U'=64.000
Sum of ranks in Column A=109.00. Sum of ranks in Column B=62.000

| Parameter: | Column A | Column B |
|---|---|---|
| Mean: | 2.883E+07 | 8381041 |
| # of points: | 9 | 9 |
| Std deviation: | 1.395E+07 | 1.851E+07 |
| Std error: | 4653075 | 6171214 |
| Minimum: | 4.900 | 34.000 |
| Maximum | 4.55E+07 | 5.60E+06 |
| Median: | 3.020E+07 | 122000 |
| Lower 95% CI: | 1.810E+07 | −5849777 |
| Upper 95% CI: | 3.956E+07 | 2.261E+07 |

Spearman Rank Correlation:
Number of points=18
Spearman r=−0.6470 (corrected for ties)
95% confidence interval: −0.8594 to −0.2439
r is significantly different than zero. The two-tailed P value is 0.0037, considered very significant.

TABLE 2

Mean data for the recovery of *Bacillus subtilis* in a 54 m³ closed system over 8 hours with UV-C treatment by the device of the invention

| Sample point in hours | Control Cfu/m³ recovered | UV-C Dosing Cfu/m³ recovered | Actual % kill % kill corrected for precipitation |
|---|---|---|---|
| 0 | 5.6E+07 | 6.1E+07 | 0.00 |
| 1 | 5.3E+07 | 1.3E+07 | 73.30 |
| 2 | 4.9E+07 | 2.7E+06 | 72.50 |
| 3 | 4.7E+07 | 6.4E+05 | 71.60 |
| 4 | 4.3E+07 | 1.4E+05 | 70.10 |
| 5 | 4.0E+07 | 2.7E+04 | 71.90 |
| 6 | 3.5E+07 | 4.5E+03 | 71.50 |
| 7 | 3.0E+07 | 5.7E+02 | 74.10 |
| 8 | 2.6E+07 | 3.9E+01 | 78.60 |

Overall % kill in 8 hours=99.9999%
Mean population precipitation rate=9.2% per hour
Mann-Whitney Test: *Bacillus subtilis*
The median values for *Bacillus subtilis* survival with no UV-C doses and UV-C doses differ significantly
The two-tailed P value is 0.0400 which is considered significant
The P value is exact.
Mann-Whitney U-statistic=17.000
U'=64.000
Sum of ranks in Column A=109.00. Sum of ranks in Column B=62.000

| Parameter: | Column A | Column B |
|---|---|---|
| Mean: | 3.589E+07 | 8612457 |
| # of points: | 9 | 9 |
| Std deviation: | 1.611E+07 | 2.009E+07 |
| Std error: | 5370817 | 6698000 |
| Minimum: | 5.600 | 39.000 |
| Maximum | 5.300E+07 | 6.100E+07 |
| Median: | 4.000E+07 | 140000 |
| Lower 95% CI: | 2.350E+07 | −6833130 |
| Upper 95% CI: | 4.827E+07 | 2.40 |

Number of points=18
Spearman r=−0.6470 (corrected for ties)
95% confidence interval: −0.8594 to −0.2439
r is significantly different than zero. The two-tailed P value is 0.0037, considered very significant

TABLE 3

Mean data for the recovery of *Bacillus megaterium* in a 54 m³ closed system over 8 hours with UV-C treatment by the device of the invention.

| Sample point in hours | Control Cfu/m³ recovered | UV-C Dosing Cfu/m³ recovered | Actual % kill % kill corrected for precipitation |
|---|---|---|---|
| 0 | 6.2E+07 | 7.3E+07 | 0.00 |
| 1 | 5.8E+07 | 2.5E+07 | 59.30 |
| 2 | 5.4E+07 | 9.8E+06 | 54.10 |
| 3 | 5.0E+07 | 2.3E+06 | 69.40 |
| 4 | 4.6E+07 | 5.0E+05 | 70.30 |
| 5 | 4.2E+07 | 1.2E+05 | 67.70 |
| 6 | 3.7E+07 | 2.2E+04 | 69.70 |
| 7 | 3.3E+07 | 2.3E+03 | 78.10 |
| 8 | 2.6E+07 | 8.4E+01 | 74.60 |

Overall % kill in 8 hours=99.9999%
Mean population precipitation rate=10.2% per hour
Mann-Whitney Test: *Bacillus megaterium*
The median values for *Bacillus megaterium* survival with no UV-C doses and UV-C doses differ significantly
The two-tailed P value is 0.0400 which is considered significant
The P value is exact.
Mann-Whitney U-statistic=17.000
U'=64.000
Sum of ranks in Column A=109.00. Sum of ranks in Column B=62.000
Number of points=18
Spearman r=−0.6470 (corrected for ties)
95% confidence interval: −0.8594 to −0.2439
r is significantly different than zero
The two-tailed P value is 0.0037, considered very significant.
The P value is approximate (exact calculations would have taken too long)

According to the data obtained, and taking into account microbial depletion not due to UV-C doses, greater than 99.999% kill rates were obtained with UV-C doses by the 8 hour mark for all organisms examined. As the initial spore challenge levels were in excess of $1.0 \times 10^7$ cfu/m³, this represents a 5 log reduction of contaminants over an 8 hour period. Furthermore in the case of each surrogate the microbial reduction obtained by UV-C doses was statistically significantly different from the level of reduction obtained purely by other factors.

Example 2

Performance of the Device of the Present Invention in the Reduction pf Airborne Microbial Contaminants in a Waste Handling Facility Trials were conducted employing the space afforded by a laboratory waste handling facility with a working volume of 216 m³. The area is employed for the containment and thermal decontamination of Class II Biological waste and has the facility both for the introduction of aerosols and, as detailed above, for the volumetric recovery of atmosphere in sample diluent.

Figure 1:
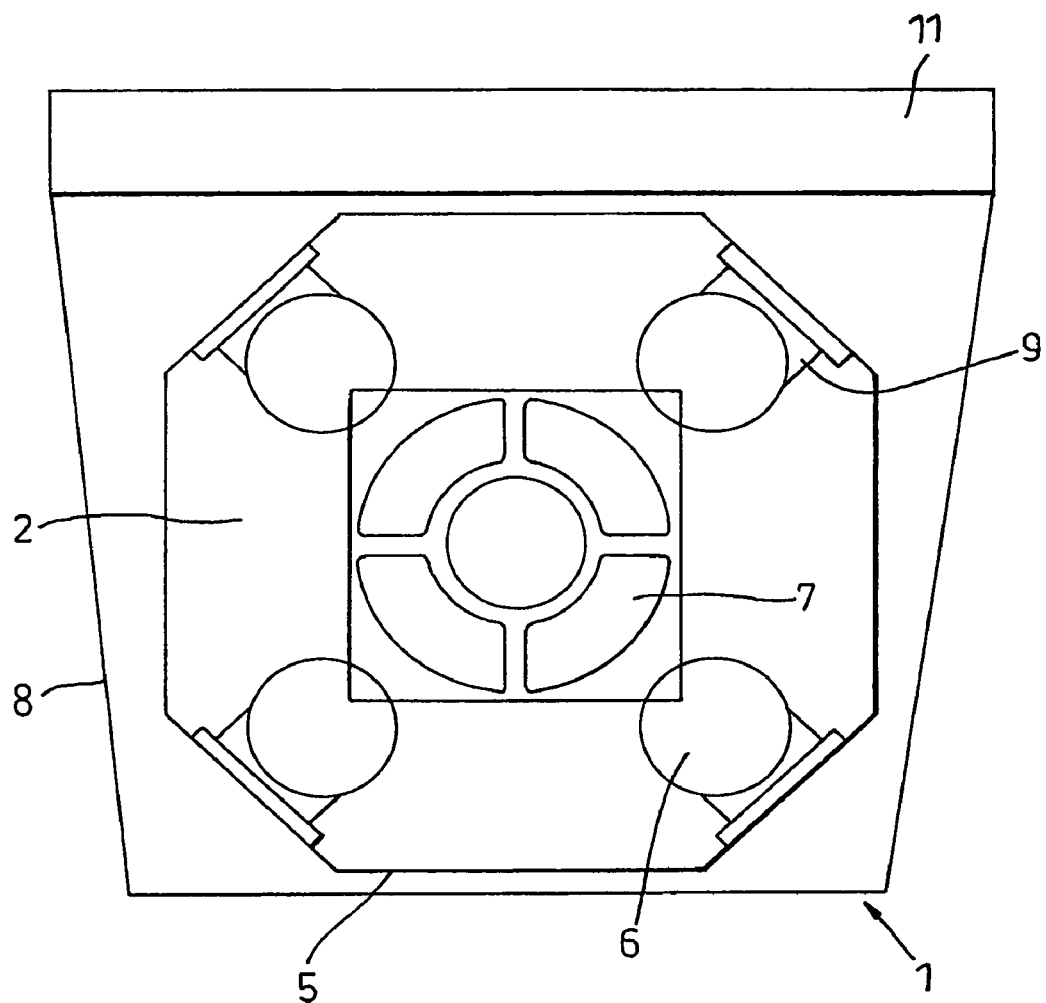
FIG. 1 is a cross section across the width of a device according to the present invention.
Figure 2:
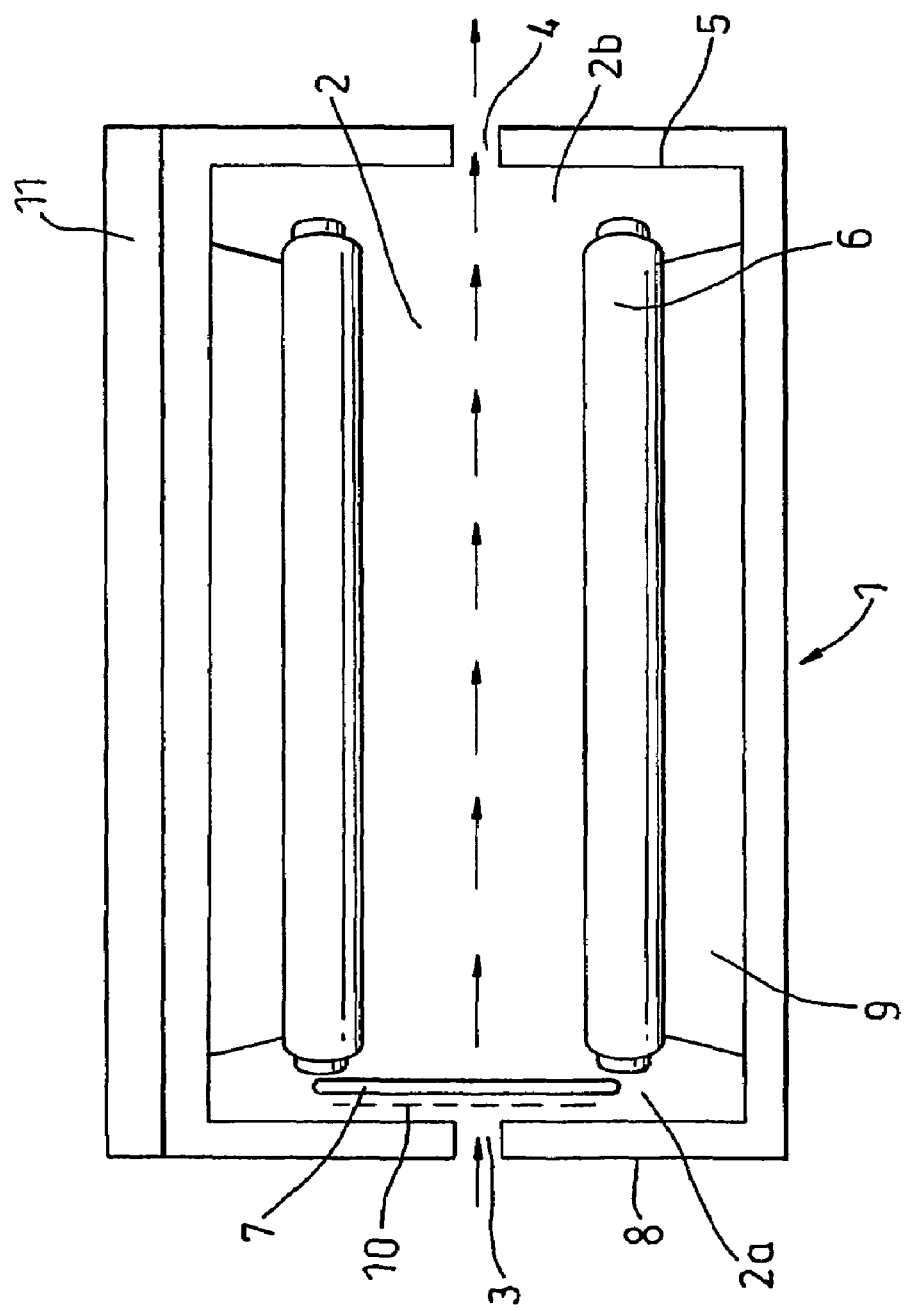
FIG. 2 is a cross section along the length of the device of FIG. 1.

The performance of the device as described above in relation to FIGS. 1 and 2 in the removal of airborne microbiological contaminants from this space was assessed.

All test organisms were obtained either as calibrated dry spore suspensions (lyophilised powder) or as calibrated mid exponential cultures in brain heart infusion. Spores were introduced and dispersed by a positive air pressure jet while in the case of vegetative cultures dispersion was achieved by use of a fogging device delivering a particle size range of 5-15 microns. As in Example 1 the test environment was conditioned for 4 hours prior to the introduction of test culture.

Throughout the trial the continued uniform atmospheric dispersion of the test organisms was maintained by a series of floor mounted industrial fans. The target level of inoculation in all cases was 10 e6/cfu/m$^3$. Dosing trials were conducted to establish loading volumes.

All trials were conducted employing mono cultures and the performance of the unit with each organism was assessed on three separate occasions. The mean data is presented. In this instance no attempt was made to establish loss of culture from the atmosphere due to precipitation. This was because Example 1 had already shown that the lethality of the device was significantly greater in comparison to removal of airborne organisms purely due to precipitation or adhesion effects in the environment.

After charging, the environment was sampled and thereafter on a four hourly basis over a 24 hour period.

The operating target was to obtain a reduction of 99.999% with respect to each target organism.

Table 4 below and the related FIG. 6 detail the range of organisms and initial atmospheric loading for each organism employed during the environmental assessment of the device. Additionally, the mean cumulative percentage reduction of atmospheric contamination incremented over the six hour period is given. The table also illustrates the sampling interval at which microbial lethality reached=>99.999%.

Example 3

Performance of the Device of the Present Invention in the Reduction of Airborne Microbial Contaminants in a Closed System The performance of the device as described above in relation to FIGS. 1 and 2 in the removal of airborne microbiological contaminants from this space was assessed.

The following organisms were employed: *Staphylococcus aureus*; NCTC 11939; carries gentamicin and Chloramphenicol plasmids/epidemic methicillin resistant strain, *Staphylococcus aureus*; NCTC 11940; epidemic methicillin resistant strain, *Staphylococcus aureus*; NCTC 11962; associated with post operative toxic shock.

In vitro trials were conducted by inoculating the surface of Tryptone Soya Agar plates with aliquots of mid exponential cell cultures. All inoculated plates were conditioned at 30° C. for 2 hours prior to UV-C treatment.

An exposed agar plate was positioned such that the surface of the plate was 50 mm from the UV-C source. Exposure of inoculated plates occurred over successive 15 second increments up to and including the 60 second mark. Cell density was estimated by deployment of sterile bores capable of obtaining 5 cm$^2$ sections of agar to a depth of 5 mm. The resulting core was subject to serial dilution with subsequent recovery of isolates on appropriate agars.

Atmospheric volumetric trials were then conducted in a microbiologically sealed PVA construction consisting of a chamber with an operating volume of 54 m$^3$. Four floor-mounted fans were employed to assist with microbial dispersion and also a silica gel unit to prevent excessive humidity build up. Pressure equalisation occurred via four apertures

TABLE 4

Performance of the device in the removal of airborne pathogens in 216 m$^3$ room space.

| Organism | Mean Organism load level cfu/m$^3$ | Time in hours; % reduction | | | | | |
|---|---|---|---|---|---|---|---|
| | | t = 0 | t = 4 | t = 8 | t = 12 | t = 16 | t = 20 | T = 24 |
| B. globigii | 4.00E+06 | 0 | 7.2 | 26.9 | 54.6 | 85.3 | 98.6 | 99.999 |
| B. subtilis | 3.60E+06 | 0 | 8.3 | 21.4 | 59.3 | 90.1 | 97.2 | 99.999 |
| B. megaterium | 7.10E+06 | 0 | 7.5 | 17.5 | 49.7 | 83.4 | 92.0 | 99.999 |
| S. typhi murium | 3.40E+06 | 0 | 17.4 | 31.2 | 91.6 | 99.999 | 99.999 | 99.999 |
| S. aureus | 2.90E+06 | 0 | 12.2 | 38.4 | 82.0 | 99.999 | 99.999 | 99.999 |
| Aspergillus niger | 3.10E+06 | 0 | 3.7 | 23.6 | 73.9 | 92.7 | 98.6 | 99.999 |
| E. coli 0157:H7 | 5.20E+06 | 0 | 19.6 | 31.7 | 94.3 | 99.999 | 99.999 | 99.999 |

Within a scope of operation of use over a 24 hour period in an environment with atmospheric contamination commencing at a level in excess of $1.0 \times 10^6$ cfu/m$^3$ the dosages of UV-C were sufficient to bring about a 99.999% reduction of all challenge organisms including *Bacillus anthracis* surrogates by the 24 hour marker.

The data illustrates that the device of the present invention represents a significant advance in atmospheric treatment. The data suggests a sensible and effective combination of airflow rate to UV-C dosage has been conceived in a system which should integrate efficiently and effectively into environmental biohazard protection systems.

secured by 0.2-micron membrane filters. This facility was equipped both for the introduction of microbial aerosols and for volumetric recovery of atmosphere in volumes of an appropriate diluent medium.

All test organisms were obtained as calibrated mid exponential cultures.

Prior to introduction of the test organisms the device was run in circuit for 4 hours to eliminate airborne contamination resident within the system. Control plates showed that all occasions this conditioning sterilisation action did reduce internal contamination to <10 cfu/m$^3$.

All studies were conducted over 8 hours and each study was repeated twice over consecutive days.

Sampling was achieved by aspiration of a 1 m³ atmosphere volume through 100 ml of diluent (Peptone Saline recovery Broth) which formed the initial test dilution. Recovery of isolates was obtained by serial dilution and plating on appropriate agars. All analyses were conducted in duplicate with appropriate controls.

Results

TABLE 5

Percentage kill (in vitro) verses exposure to UV-C with three strains of *Staphylococcus aureus*

| | | Exposure time cfu/cm2 agar/recovered | | | | | |
|---|---|---|---|---|---|---|---|
| Organism | N | T = sec 0 | T = sec 15 | T = sec 30 | T = sec 45 | T = sec 60 | % Reduction |
| *S. aureus* | | | | | | | |
| 11939 | 4 | 9.30E+07 | 5.20E+05 | 1300 | 4 | 0 | >99.999 |
| 11940 | 4 | 4.60E+07 | 6.10E+05 | 2400 | 9 | 0 | >99.999 |
| 11962 | 4 | 1.90E+07 | 8.30E+04 | 670 | 3 | 0 | >99.999 |

TABLE 6

UV-C log reduction of three strains of *Staphylococcus aureus*

| Sample point in hours | UV-C cfu/m3 recovered 11939 | UV-C Log Kill 11939 | UV-C cfu/m3 recovered 11940 | UV-C Log Kill 11940 | UV-C cfu/m3 recovered 11962 | UV-C Log Kill 11962 |
|---|---|---|---|---|---|---|
| 0 | 3.30E+08 | 0.0 | 4.20E+08 | 0.0 | 6.10E+08 | 0.0 |
| 1 | 1.60E+08 | 0.3 | 2.70E+08 | 0.1 | 3.40E+08 | 0.0 |
| 2 | 4.50E+07 | 0.9 | 6.20E+07 | 0.7 | 2.70E+07 | 1.1 |
| 3 | 1.60E+07 | 1.3 | 8.40E+06 | 1.6 | 1.20E+07 | 1.4 |
| 4 | 3.20E+06 | 2.0 | 9.20E+05 | 2.6 | 5.30E+06 | 1.8 |
| 5 | 9.20E+05 | 2.6 | 7.30E+04 | 3.7 | 3.00E+05 | 3.0 |
| 6 | 8.60E+04 | 3.6 | 2.00E+04 | 4.2 | 2.80E+04 | 4.1 |
| 7 | 7.40E+02 | 5.6 | 3.90E+02 | 5.9 | 1.70E+02 | 6.3 |
| 8 | 8.00E+01 | 6.6 | 4.00E+01 | 6.9 | 2.00E+01 | 7.2 |

Treatment by the device of the present invention is clearly shown to be capable of bringing about a greater than 99.999% reduction of Staphylococcal numbers within one minute. This was achieved with numbers of organisms far in excess of those that would normally be present in a high care medical environment.

The device is also capable of achieving between 6.6 and 7.2 log cycles of kill over an eight hour period. Again this was demonstrated by employing very high numbers of organisms in atmospheric dispersion.

Example 4

Performance of the Device of the Present Invention in the Reduction of Airborne Microbial Contaminants in a Hospital Unit A field trial was conducted in a four-bed high dependency unit of a London Hospital. The unit volume measured 248 m³ and contained four beds and a clinical reception area. The unit was temperature controlled with air handling units fed from external ducts with EU4 primary and EU8 secondary filtering.

The performance of two devices as described above in relation to FIGS. 1 and 2 was assessed by fitting them in the ward and sampling the air several times per day using Cassala air sampling units. This sampling unit employs the technique of impacting a known volume (200 L) of air onto the surface of a sterile rotating agar plate in a manner that evenly distributes the air borne micro-organisms over the surface of a plate.

The agars employed in this trial were allocated to afford the recovery of a wide range of aerobic airborne bacteria and spores including airborne class II pathogens. A combination of non-selective, elective and selective solid media was employed which included; Typtone soya agar, Violet red bile agar, Violet red bile glucose agar, Brucella medium, Rogosa agar, C.L.E.D agar, MRS agar, Baird Parker agar, DNA-ase agar, and modified forms of these agars.

A control period of 7 days was implemented with the devices switched off (Period A), followed by a test period of a further 7 days with them switched on (Period B). Test plates from the Cassala units were removed, incubated under optimal conditions to afford recovery of visible colonies and examined for evidence of colony forming units. All isolates were grouped and identified according to a scheme involving Gram strain and a series of morphological, biochemical and serological reactions.

In addition the background level of contamination was measured by sampling the air input to the air-handling units on the roof of the building to establish correlation between air input and the effectiveness of the building filter system.

Results

The Mann-Whitney non-parametric T-test has been used as the statistical tool to test significances where applicable for population means.

Data recovered for the mean total viable aerobic count (TVC) in 200 $L^{-1}$ of ward atmosphere for each day is presented in Table 7 for both periods A and B. In the same table the respective daily mean counts for total Gram +ve and Gram −ve isolates.

As can be seen, in respect of the Total Viable Count data a highly significant difference exists at the 95 probability level indicating that the average daily TVC cfu/200 $L^{-1}$ of air for period B was lower than period A. In considering the data obtained for Gram +ve and Gram −ve populations a highly significant difference also exists at the 95 probability level that the average counts for both populations is lower during the period (B) when the device was operating.

TABLE 7

Mean sampling data for categories of organisms isolated from the atmosphere of a high care ward over 2 consecutive 7 day periods with and without the operation of the device

| Day | State | Internal TVC cfu 200 $L^{-1}$ | Internal Gram −ve cfu 200 $L^{-1}$ | Internal Gram +ve cfu 200 $L^{-1}$* | Internal *S. aureus* cfu 200 $L^{-1}$* |
|---|---|---|---|---|---|
| 1 | OFF | 174 | 93 | 81 | 0 |
| 2 | OFF | 231 | 176 | 55 | 0 |
| 3 | OFF | 288 | 144 | 144 | 7 |
| 4 | OFF | 173 | 87 | 86 | 0 |
| 5 | OFF | 324 | 219 | 105 | 3 |
| 6 | OFF | 461 | 303 | 158 | 11 |
| 7 | OFF | 211 | 113 | 98 | 0 |
| 1 | ON | 192 | 63 | 129 | 0 |
| 2 | ON | 78 | 24 | 54 | 0 |
| 3 | ON | 94 | 28 | 66 | 0 |
| 4 | ON | 161 | 96 | 65 | 0 |
| 5 | ON | 67 | 31 | 36 | 0 |
| 6 | ON | 83 | 48 | 35 | 0 |
| 7 | ON | 94 | 32 | 62 | 0 |

*confirmed bacterial isolates

| | | | | |
|---|---|---|---|---|
| Mean UV-C off | 266 | 162 | 104 | 3 |
| | | 61% | 39% | 1% |
| Mean UV-C on | 110 | 46 | 64 | 0 |
| | | 42% | 58% | 0% |

Taking into account the effect of external intake air microbiological quality, data for Total Viable Count and those obtained for the levels of Gram +ve and Gram –ve contamination are given in Table 8. All categories of count are significantly greater at the 95% probability level than those obtained in the ward irrespective of whether or not the UV-C device was operating.

Per force the efficiency of the device was measured over two periods (A and B). During Period A (UV-C off) there were lower levels of microbiological input from the external air intake than during period B. However, a significant reduction of microbial loading was still shown in the ward during period B (UV-C on), when the challenge from external air input was greater.

TABLE 8

Mean sampling data for categories of organisms isolated from the atmosphere of a high care ward External air intake over 2 consecutive 7 day periods showing the TVC data described in Table 7

| Day | intake TVC cfu.200 liters$^{-1}$* | intake Gram –ve cfu.200 liters$^{-1}$* | intake Gram +ve cfu.200 liters$^{-1}$* | intake S. aureus cfu.200 liters$^{-1}$* |
|---|---|---|---|---|
| 1 | 636 | 438 | 198 | 2 |
| 2 | 541 | 332 | 209 | 3 |
| 3 | 506 | 290 | 216 | 0 |
| 4 | 682 | 386 | 296 | 8 |
| 5 | 608 | 327 | 281 | 90 |
| 6 | 930 | 571 | 359 | 114 |
| 7 | 746 | 459 | 287 | 0 |
| 8 | 790 | 408 | 382 | 1 |
| 9 | 870 | 511 | 359 | 3 |
| 10 | 943 | 633 | 310 | 3 |
| 11 | 782 | 440 | 342 | 6 |
| 12 | 907 | 605 | 302 | 0 |
| 13 | 830 | 430 | 400 | 2 |
| 14 | 734 | 380 | 354 | 1 |

*confirmed bacterial isolates

| | | | | |
|---|---|---|---|---|
| Mean UV-C off | 664 | 400 | 264 | 31 |
| | | 60% | 40% | 5% |
| Mean UV-C on | 837 | 396 | 290 | 31 |
| | | 47% | 35% | 4% |

Included within the observed levels of organisms during Period A was the presence of *Staphylococcus aureus*. During the second period, Period B with the machine switched on no *Staphylococcus aureus* was detected.

Over the two periods, it was demonstrated that there was a significant (59%) reduction in the bio-burden even when challenged from a higher external input load.

The invention claimed is:

1. A fluid purification device (1), which comprises a chamber (2) having an inlet (3) and an outlet (4), a fluid mover (7) and four elongate UV-C light sources (6), wherein said fluid mover causes fluid to pass through the chamber from the inlet towards the outlet, a volume of the chamber and a speed of the fluid movement caused by the fluid mover being such that the fluid has a residence time in the chamber of greater than 1.0 seconds and, said light sources being provided in the chamber in an arrangement such that the fluid passes along their length and such that each light source forms an elongate edge of a square prism, wherein the fluid mover is a fan.

2. The fluid purification device according to claim 1 wherein the four elongate UV-C light sources are of a wattage and a distance from a center of the chamber such that the level of UV-C energy at any point within the chamber is at least 15000 µWscm$^{-2}$.

3. The fluid purification device according to claim 1 wherein the UV-C light sources are 25 W input UV-C light sources and are arranged so as to be at a distance from a center of the chamber of 50 mm or less.

4. The fluid purification device according to claim 1 wherein the elongate UV-C light sources are positioned 30 mm or less from an inner wall of the chamber.

5. The fluid purification device according to claim 1 wherein the UV-C light sources emit germicidal UV-C light in the range of from 240 to 280 nm.

6. The fluid purification device according to claim 1 wherein the UV-C light sources have a peak emission in the range of from 250 to 260 nm.

7. The fluid purification device according to claim 6 wherein the UV-C light sources have a peak emission at 253.7 nm.

8. The fluid purification device according to claim 1 wherein the UV-C light sources do not emit radiation in the range of from 170 nm to 200 nm.

9. The fluid purification device according to claim 8 wherein the UV-C light sources do not produce any radiation at a wavelength below 240 nm.

10. The fluid purification device according to claim 1 wherein the volume of the chamber is adapted and the fluid mover is adapted such that fluid passing through the device is treated by UV-C radiation for greater than 1.0 s.

11. The fluid purification device according to claim 10 wherein the volume of the chamber is adapted and the fluid mover is adapted such that fluid passing through the device is treated by UV-C radiation for 1.2 s or more.

12. The fluid purification device according to claim 11 wherein the volume of the chamber is adapted and the fluid mover is adapted such that fluid passing through the device is treated by UV-C radiation for 1.4 s or more.

13. The fluid purification device according to claim 12 wherein the volume of the chamber is adapted and the fluid mover is adapted such that fluid passing through the device is treated by UV-C radiation for 1.7 s or more.

14. The fluid purification device according to claim 1 wherein the chamber has inner surfaces (5) that are UV-C reflective.

15. The fluid purification device according to claim 14 wherein the inner surfaces of the chamber have a coefficient of reflection of 60% or more for germicidal UV-C wavelengths.

16. The fluid purification device according to claim 15 wherein the inner surfaces of the chamber have a coefficient of reflection of 70% or more for germicidal UV-C wavelengths.

17. The fluid purification device according to claim 14 wherein the inner surface of the chamber is aluminum.

18. The fluid purification device according to claim 1 further comprising one or more filters (10).

19. The fluid purification device according to claim 18 wherein at least one filter is provided at or near the beginning of the fluid flow through the device.

20. The fluid purification device according to claim 19 wherein the at least one filter is disposed at or immediately adjacent the inlet of the chamber, such that the fluid entering the chamber through the inlet subsequently passes through the filter.

21. The fluid purification device according to claim 18 wherein at least one of the one or more filters has a mesh size of 13.8 pores/cm.

22. The fluid purification device according to claim 1 further comprising an outer casing (8) within which the chamber is located.

23. A method of reducing the level of microbial contaminants in a fluid comprising the steps of:
providing a fluid purification device comprising:
a chamber (2) having an inlet (3) and an outlet (4),
a fluid mover (7) that causes the fluid to pass through the chamber from the inlet to the outlet, wherein a volume of the chamber and a speed of the fluid movement caused by the fluid mover results in the fluid having a residence time in the chamber of greater than 1.0 second; and
four elongate UV-C light sources (6) arranged such that each light source forms an elongate edge of a square prism, such that the fluid passes along a length of the UV-C light sources, and
passing the fluid through the chamber of the fluid purification device such that the fluid is irradiated with germicidal UV-C light from the UV-C light sources, wherein the fluid is a gas.

24. The method according to claim 23 wherein the fluid is air.

25. The method according to claim 23 wherein the fluid is irradiated with germicidal UV-C light from the UV-C light sources for greater than 1.0 s.

26. The method of claim 23 wherein a level of UV-C light in the chamber is at least 15000 $\mu Wscm^{-2}$.

27. The method of claim 23 wherein the UV-C light sources are at least 25 W input and are disposed 50 mm or less from a center of the chamber.

28. The method of claim 23 wherein the UV-C light sources emit radiation in the range of about 240 to 280 nm.

29. The method of claim 23 wherein an inner surface of the chamber has a coefficient of reflection of 60% or more for germicidal UV-C wavelengths.

30. The method of claim 29 wherein the inner surface of the chamber is aluminum.

31. The method of claim 23 wherein the fluid purification device further comprises at least one filter having a mesh size of 13.8 pores/cm.

32. A purification device for irradiating a fluid with a germicidal UV-C light, comprising:
a chamber having an inlet and an outlet;
a fluid mover that causes the fluid to pass through the chamber from the inlet to the outlet, wherein a volume of the chamber and a speed of the fluid movement caused by the fluid mover results in the fluid having a residence time in the chamber of greater than 1.0 second; and
four elongate UV-C light sources each having at least a 25 W input and disposed 50 mm or less from a center of the chamber, arranged such that each light source forms an elongate edge of a square prism, such that the fluid passes along a length of the UV-C light sources, wherein the fluid mover is a fan.

33. A purification device for irradiating a fluid with a germicidal UV-C light, comprising:
a chamber having an inlet and an outlet;
a fluid mover that causes the fluid to pass through the chamber from the inlet to the outlet, wherein a volume of the chamber and a speed of the fluid movement caused by the fluid mover results in the fluid having a residence time in the chamber of greater than 1.0 second; and
four elongate UV-C light sources providing a level of UV-C light in the chamber of at least 15000 $\mu Wscm^{-2}$ and arranged such that each light source forms an elongate edge of a square prism, such that the fluid passes along a length of the UV-C light sources, wherein the fluid mover is a fan.

34. A fluid purification device (1), which comprises a chamber (2) having an inlet (3) and an outlet (4), an outer casing (8) within which the chamber is located, a fluid mover (7) and four elongate UV-C light sources (6), wherein said fluid mover causes fluid to pass through the chamber from the inlet towards the outlet, a volume of the chamber and a speed of the fluid movement caused by the fluid mover being such that the fluid has a residence time in the chamber of greater than 1.0 seconds and, said light sources being provided in the chamber in an arrangement such that the fluid passes along their length and such that each light source forms an elongate edge of a square prism.

* * * * *